US006630092B2

(12) United States Patent
Avalle

(10) Patent No.: US 6,630,092 B2
(45) Date of Patent: Oct. 7, 2003

(54) PROCESS FOR THE PROVISION OF VARIEDLY COLORED INCISIONS ON COMPACT OR POURED COSMETIC PRODUCTS

(75) Inventor: Nadia Avalle, Milan (IT)

(73) Assignee: Intercos Italia S.p.A., Milan (IT)

( * ) Notice: Subject to any disclaimer, the term of this patent is extended or adjusted under 35 U.S.C. 154(b) by 41 days.

(21) Appl. No.: 09/852,618

(22) Filed: May 11, 2001

(65) Prior Publication Data

US 2002/0121284 A1 Sep. 5, 2002

(30) Foreign Application Priority Data

Mar. 5, 2001 (IT) .................................... MI2001A0448

(51) Int. Cl.[7] .......................... B23K 26/06; A61K 7/02

(52) U.S. Cl. ...................... 264/400; 264/139; 264/245; 264/246; 264/482; 219/121.66; 219/121.69

(58) Field of Search ................................ 264/400, 482, 264/139, 245, 246, 132, 134; 219/121.65, 121.66, 121.68, 121.69

(56) References Cited

U.S. PATENT DOCUMENTS

| | | | | | |
|---|---|---|---|---|---|
| 4,753,863 | A | * | 6/1988 | Spanjer | 430/138 |
| 4,861,620 | A | * | 8/1989 | Azuma et al. | 427/53.1 |
| 6,180,048 | B1 | * | 1/2001 | Katori | 264/400 |
| 6,183,762 | B1 | * | 2/2001 | Deckers et al. | 424/401 |
| 6,383,721 | B1 | * | 5/2002 | Kamimura et al. | 430/320 |

FOREIGN PATENT DOCUMENTS

| | | | |
|---|---|---|---|
| DE | 19730887 A1 | | 1/1999 |
| IT | MI2000A002686 | | 12/2000 |
| JP | 62-164610 | | 7/1987 |
| JP | 03-288624 | * | 12/1991 |
| JP | 2000-247832 | * | 9/2000 |
| JP | 2000-300333 | * | 10/2000 |

* cited by examiner

*Primary Examiner*—Stefan Staicovici
(74) *Attorney, Agent, or Firm*—Jacobson Holman PLLC

(57) ABSTRACT

A process for the provision of variedly colored incisions on a cosmetic product is described, that comprises the steps of superimposing a colored thin surface layer (8) onto the cosmetic product (1) and utilising a laser beam (5) directed towards said surface layer (1) and said cosmetic products (1) as an incident tool.

4 Claims, 1 Drawing Sheet

PROCESS FOR THE PROVISION OF VARIEDLY COLORED INCISIONS ON COMPACT OR POURED COSMETIC PRODUCTS

DESCRIPTION

The present invention concerns a procedure for the provision of variedly coloured incisions on compact or poured cosmetic products.

By the term "compact cosmetic products" those powder cosmetic products are herein meant which have been transformed into a compact powder by means of a process of pressing into an appropriate container.

By the term "poured cosmetic products" those products are instead meant which, after a melting process, get poured and metered into a container.

For many years there have been on the market make-up products that have surface relieves or incisions that can be provided by several methods so as to generate relieves or incisions having very variable shape, sizes and depths.

In the Italian patent application MI2000A002686 filed on Dec. 13, 2000 in the name of the same Applicant a new process for the provision of incisions on compact or poured cosmetic products is described, which utilises a laser beam directed towards the surface of the cosmetic product as an incising tool. Such laser beam burns and removes the surface portions of the cosmetic product with which it gets into contact, thus leaving the cosmetic product incised. In very short working times it is possible to provide shapes that are even very complex and with substantially unlimited design and have very clear details and no mutual interferences, even if very close.

Now it has been noticed that the aesthetic effect resulting from such process of incision can be additionally improved up to creating incisions having very pleasant coloration, colour gradient and chromatic contrasts.

SUMMARY OF THE INVENTION

This is obtained, according to the present invention, by superimposing a thin coloured surface layer onto the cosmetic product and by incising both said layer and the cosmetic product underneath according to desired lines and depths.

In this way, by varying the colour and/or the colour gradient and/or the distribution of the colours of the surface layer and by incising the aforesaid layer and the cosmetic products below, that are variedly coloured too, according to variable lines and patterns and also with variable depths of incising, it is possible to obtain extremely variable and pleasant designs and chromatic effects.

BACKGROUND OF THE INVENTION

Figure 1:
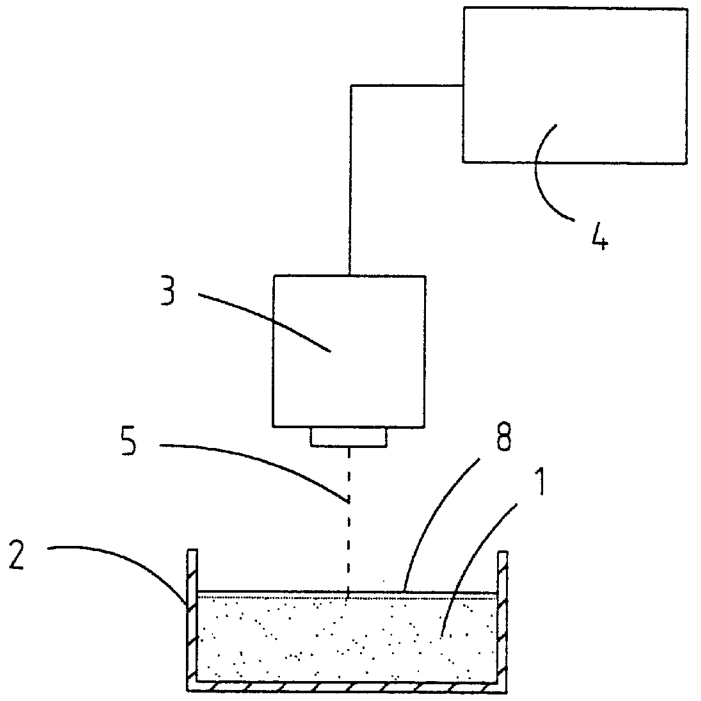
Figure 2:
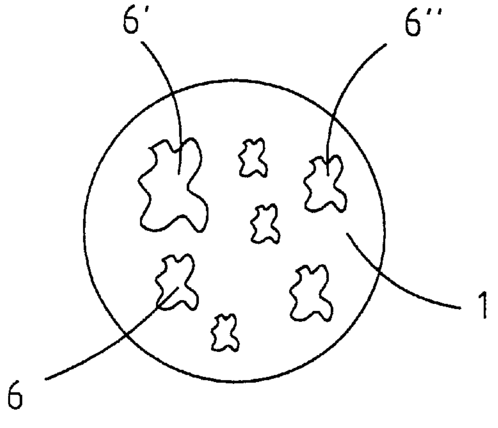
Figure 3:
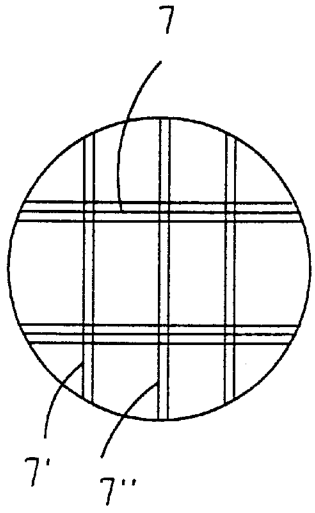

The incising process according to the invention is schematically exemplified in the enclosed drawings, in which:

FIG. 1 schematically shows a laser source controlled by a computer during the incising stage of the surface of a cosmetic product provided with a coloured thin surface layer;

FIG. 2 shows in top plan a possible surface incision designs as marks that can be made with the process according to the invention; and FIG. 3 shows in top plan a cosmetic product with incision realised as lines that cross one another.

DESCRIPTION OF THE INVENTION

In Figure a 1 cosmetic product 1 of any colour, housed inside a container 2 and provided with a thin surface layer 8, in its turn coloured in a uniform or variable way from one zone to the other, is located under a laser source 3, which a computer 4 controls in order to have it emit a laser beam 5 with angle variable according to the design of the incision to be realised, with any desired depth, on the surface of the cosmetic product.

FIG. 2 shows as an example a cosmetic product with incision realised as marks 6, 6' and 6" separate from each other. These marks can have different design and different depth, and above all various colour depending on the colour of the cosmetic product 1, of the colour of surface layer 8 and the depth of incision itself.

FIG. 3 shows as an example a cosmetic product with incision realised as lines 7, 7' and 7" that cross one another. Also for these lines the previous considerations regarding the variability of the design, depth and colour hold true. Naturally many other, even more complex designs and with the most different chromatic effects, can be realised with the same technique.

To the purpose of the desired incision it is indifferent that the cosmetic product is a compact or poured type.

What is claimed is:

1. A process for providing a variedly colored surface on a cosmetic product having variable design and chromatic effects, comprising the steps of:

covering the variedly colored surface of the cosmetic product with a variedly colored thin layer; and incising both the colored thin layer and the cosmetic product underneath by a laser beam directed toward the colored thin layer and the variedly colored surface according to variable lines, patterns or depths.

2. The process according to claim 1, wherein said laser beam is emitted by a laser source controlled by a computer.

3. The process according to claim 1, wherein said cosmetic products is a compact type one.

4. The process according to claim 1, wherein said cosmetic products is a poured type one.

* * * * *